United States Patent
Bagolini et al.

(10) Patent No.: US 6,693,215 B2
(45) Date of Patent: Feb. 17, 2004

(54) PROCESS FOR THE PREPARATION OF SALTS OF L-CARNITINE AND ALKANOYL L-CARNITINE WITH MUCIC ACID

(75) Inventors: Carlo Alberto Bagolini, Pomezia (IT); Angelo De Luca, Pomezia (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 0 days.

(21) Appl. No.: 10/203,565
(22) PCT Filed: Feb. 9, 2001
(86) PCT No.: PCT/IT01/00056
   § 371 (c)(1),
   (2), (4) Date: Oct. 28, 2002
(87) PCT Pub. No.: WO01/58850
   PCT Pub. Date: Aug. 16, 2001
(65) Prior Publication Data
   US 2003/0130539 A1 Jul. 10, 2003
(51) Int. Cl.[7] .................. C07C 229/00; A61K 31/95
(52) U.S. Cl. .................. 562/553; 514/561; 514/556
(58) Field of Search .................. 514/561, 556; 560/196; 562/512, 553, 590

(56) References Cited

U.S. PATENT DOCUMENTS 5,952,379 A    9/1999   Fassi
6,271,258 B1 * 8/2001   Fassi .......................... 514/561

* cited by examiner

*Primary Examiner*—James O. Wilson
*Assistant Examiner*—Karl J. Puttlitz
(74) *Attorney, Agent, or Firm*—Nixon & Vanderhye P.C.

(57) ABSTRACT

An improved process is described for the industrial preparation of L-carnitine or alkanoyl L-carnitine mucate, which allows operations in a homogeneous phase in conditions of greater dilution, in a normal chemical reactor with stirring, in a batch process.

3 Claims, No Drawings

PROCESS FOR THE PREPARATION OF SALTS OF L-CARNITINE AND ALKANOYL L-CARNITINE WITH MUCIC ACID

The invention described herein relates to an improved process for the industrial preparation of mucates of L-carnitine and of alkanoyl L-carnitines.

It has been known for some time that L-carnitine, its alkanoyl derivatives and their salts lend themselves to various therapeutic and nutritional uses.

It is also known that L-carnitine and its alkanoyl derivatives are extremely hygroscopic compounds and are poorly stable when they present themselves as inner salts. This leads to complex problems of processing, stability and storage of both the raw materials and the finished products.

U.S. Pat. No. 5,952,379 (Sigma-Tau Industrie Farmaceutiche Riunite) describes the mucates of L-carnitine and the alkanoyl L-carnitines as non-hygroscopic salts.

U.S. Pat. No. 5,952,379 describes the above-mentioned mucates as salts of L-carnitine or of the alkanoyl L-carnitines in which the ratio of L-carnitine or alkanoyl L-carnitine to mucic acid is 2:1.

These salts do not present the drawbacks of hygroscopicity, poor storage stability, difficult processing and the packaging problems of the corresponding inner salts, and release no traces of trimethylamine even in extreme storage conditions (in terms of duration, temperature, and percentage relative humidity). Moreover, these salts present the same anion in both the L-carnitine salt and the lower alkanoyl carnitine salts, particularly acetyl L-carnitine.

The process described in U.S. Pat. No. 5,952,379 uses as the starting compound the inner salt of L-carnitine or of an alkanoyl L-carnitine.

The preparation of the starting compound, in the exemplary case of acetyl L-carnitine, involves the following steps:
a) dissolving acetyl L-carnitine chloride in water;
b) ion exchange to yield acetyl L-carnitine inner salt in aqueous solution;
c) distillation of the water until a 60% weight by weight aqueous solution is obtained;
d) azeotropic distillation;
e) precipitation with acetone;
f filtration of the precipitate;
g) drying to obtain acetyl L-carnitine inner salt powder.

The process described in U.S. Pat. No. 5,952,379 allows the preparation of L-carnitine or of an alkanoyl L-carnitine mucate, as described here below.

A suitable amount of starting product in the form of inner salt is mixed in the minimum amount of water necessary for obtaining a mixture of pasty or semiliquid consistency; mucic acid is added to the paste at ambient temperature in a molar amount which is half the molar amount of the starting product, and the mixture thus obtained is fully amalgamated; the solidification/dehydration reaction is then carried out leaving the reaction mixture in air, with a relative humidity content not greater than 50%, or, accelerating the solidification/dehydration reaction by means of appropriate drying techniques. The final solid product can also be ground, if so required, to yield the salt in the form of a powder or granulate.

When the preparation process of the mucates described in the above-mentioned U.S. Pat. No. 5,952,379 is carried out on a large scale, equipment should be used which is suitable for the mixing of pasty or semisolid phases. Equipment of this kind is known in the field to which the invention described herein refers and the choice of such equipment falls within the normal range of technical knowledge of the average expert in the field. For example, rotary-arm mixers can be used, or other equivalent means, including those described in related fields.

At pilot level preparations were carried out on a scale of 1–50 kg using the method described in U.S. Pat. No. 5,952,379.

A suitable amount of acetyl L-carnitine inner salt was suspended in a small amount of water and mixed until a homogeneous syrup was obtained; a suitable amount of finely ground mucic acid was added (molar ratio 2:1 of acetyl L-carnitine to mucic acid) and the mixture thus obtained was amalgamated using rotary-arm mixers. The reaction mass was mixed until it hardened.

A compact solid was obtained which after drying, grinding and further drying yielded acetyl L-carnitine mucate powder.

When carrying out the process described in U.S. Pat. No. 5,952,379 it was found that:

the raw material envisaged as the starting material is L-carnitine inner salt or an alkanoyl L-carnitine inner salt, i.e. compounds which are expensive and notoriously hygroscopic, unstable and easily degradable unless stored in suitable environments in conditions of controlled temperature and humidity. Moreover, the inner salts used are obtained from the respective chlorides, with a process that adds an additional cost to the process of preparation of L-carnitine mucate or of alkanoyl L-carnitine mucate;

the reaction, which takes place in a heterogeneous phase in a highly viscous medium (mixture of acetyl L-carnitine and water), is achieved only thanks to efficient stirring (a process controlled by a dynamic regimen) which can be achieved on an industrial scale only by bringing to bear very considerable mechanical power;

after the addition of mucic acid, the amalgamated mass hardens rapidly; this process can be performed only if one uses equipment capable of supporting the mechanical stress required to guarantee efficient mixing and proper handling of the reacted mass. If the pressures exerted are not enough to reproduce the dynamic behaviour of the system, the reaction may be incomplete, with the result that a simple mechanical mixture may be obtained consisting of the two reactants and partly reacted product, or, at any rate, an uneconomic salt yield.

To be suitable for use in the subsequent transformations, e.g. formulation in dosage units, the solid block obtained needed to be broken up, dried and crushed.

An improved process has now been found, and constitutes the object of the invention described herein, for the preparation of L-carnitine or alkanoyl L-carnitine mucates, allowing their preparation on a large scale without having to resort to the use of complex, expensive equipment such as mixers or other suitable equivalent means.

The process according to the invention described herein comprises as the starting product L-carnitine chloride or an alkanoyl L-carnitine chloride, preferably acetyl L-carnitine or propionyl L-carnitine chloride, these being compounds that are known to be more stable and more economic.

Moreover, this process is carried out by means of a homogeneous-phase reaction in conditions of higher dilution, in a normal chemical reactor with stirrer, in a batch process.

Thanks to this new process, both the problems relating to the use of expensive and unstable starting materials and those relating to the equipment to be used have been overcome.

The process according to the invention can be schematically represented in the following reaction scheme:
a) dissolving of L-carnitine chloride or alkanoyl L-carnitine chloride in water;
b) ion exchange with a weak liquid anion exchanger resin, functionalised with secondary amino groups, to yield L-carnitine or alkanoyl L-carnitine inner salt in aqueous solution;
c) distillation of the water until a 60% weight by weight aqueous solution is obtained;
d) salification reaction with mucic acid;
e) precipitation with acetone;
f) isolation of the precipitate.

The subject matter of the invention described herein is therefore a process for the preparation of L-carnitine mucate or of alkanoyl L-carnitine mucates with general formula (I)

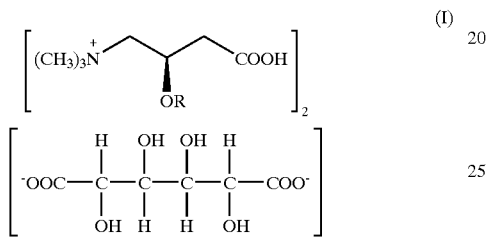

where R is hydrogen or a straight or branched alkanoyl group with 2–6 carbon atoms,
comprising the steps of:
(a) dissolving the L-carnitine chloride or alkanoyl L-carnitine chloride in distilled water at a temperature ranging from ambient temperature to 100° C. to yield a solution;
(b) treating the step (a) solution with a suitable exchanger resin to yield L-carnitine or alkanoyl L-carnitine inner salt in aqueous solution;
(c) distilling the step (b) L-carnitine inner salt or alkanoyl L-carnitine inner salt until an aqueous solution containing 60% weight by weight of L-carnitine inner salt or alkanoyl L-carnitine inner salt is obtained;
(d) adding to the step (c) solution a suitable amount of mucic acid to yield a solution in which the mucic acid is dissolved together with the L-carnitine or alkanoyl L-carnitine;
(e) adding to the step (d) solution a suitable amount of organic solvent as a precipitating agent; the two liquid phases (aqueous and acetonic) are transformed under stirring into a suspension of the salt;
(f) isolating the step (e) precipitate; and, optionally
(g) drying the step (f) precipitate.

Step (b) of the reaction scheme can be suitably carried out using a weak liquid anion exchanger resin, functionalised with secondary amino groups, or with a solid or liquid anion exchanger resin functionalised as a quaternary ammonium salt or polyamine or equivalent substance.

Step (e) of the reaction scheme can also be suitably carried out by using as precipitating agents ethers (e.g. THF), other ketones, esters (e.g. ethyl acetate), ketoesters (e.g. ethyl acetoacetate), and alcohols (e.g. isobutyl alcohol).

The isolation of the end product (step (f)) is carried out using the normal techniques available to the average expert in the field. One preferred technique is filtration, but other equivalent techniques are equally suitable. The end product can be further dried to the degree of relative humidity desired; it can be recrystallised, or, if regarded as desirable, though not necessary for the normal uses for which the product is envisaged, it can be further purified, for example, in order to obtain a standard. On the whole, in addition to the advantages apparent to the expert in the field, the invention described herein solves the above-mentioned problems relating to the equipment to be used in carrying out the salification reaction on a large scale, and in particular solves the technological problems relating to the breaking down and crushing of the solid mass, when necessary, as well as to its handling and drying.

One preferred embodiment of the invention relates to acetyl L-carnitine mucate (2:1) and propionyl L-carnitine mucate (2:1).

The following examples further illustrate the invention.

EXAMPLE 1

100 kg of acetyl L-carnitine chloride were dissolved in 400 L of distilled water.

The solution thus obtained was subject to ion exchange with 1500 L of Amberlite LA2 anion exchanger resin/hexane (1:1).

The aqueous phase thus obtained was concentrated in a 1500 L steel reactor at 10–20 Torr (0.013–0.026 bar; 1333–2666 Pa) absolute pressure, and at an inner temperature of 20–25° C., until a 60% weight by weight acetyl L-carnitine inner salt solution was obtained.

42.750 kg of mucic acid were loaded into the same reactor and the solution thus obtained was stirred for 15 minutes.

800 L of acetone were added; initially an oily aqueous phase was separated below the acetone phase, and then, after leaving the solution to stir overnight a filterable crystalline solid was separated.

The solid was filtered, washed with acetone and dried overnight at 35° C., obtaining 123 kg of a white solid (molar yield=92%).

Table 1 gives a number of analytical data for the compound obtained.

TABLE 1

| Aspect | Powder |
|---|---|
| Colour | White |
| Water solubility | Poorly soluble |
| Content in water (%)- K.F. | 3.5 |
| pH | 3.8 |
| HPLC | Compliant |
| HPLC titer (%) | 63.8 |
| Acetyl L-carnitine inner salt | |

EXAMPLE 2

In the same way as in example 1, with the obvious variants as appropriate, mucates of L-carnitine, propionyl L-carnitine, butyryl L-carnitine and isovaleryl L-carnitine were prepared.

What is claimed is:
1. A process for the preparation of L-carnitine mucate or of an alkanoyl L-carnitine mucate with general formula (I)

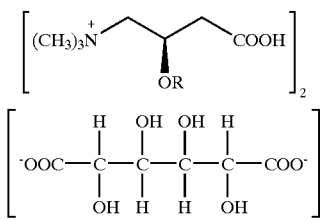

$$\begin{bmatrix} (CH_3)_3\overset{+}{N} & & COOH \\ & OR & \end{bmatrix}_2 \quad (I)$$

$$\begin{bmatrix} & H & OH & OH & H & \\ ^-OOC- & \overset{|}{\underset{|}{C}}- & \overset{|}{\underset{|}{C}}- & \overset{|}{\underset{|}{C}}- & \overset{|}{\underset{|}{C}}- & COO^- \\ & OH & H & H & OH & \end{bmatrix}$$

where R is hydrogen or a straight of branched alkanoyl group with 2–6 carbon atoms, comprising the steps of:
(a) dissolving L-carnitine chloride or alkanoyl L-carnitine chloride in distilled water at a temperature ranging from ambient temperature to 100° C. to yield a solution;
(b) treating the step (a) solution with a suitable exchanger resin to yield L-carnitine or alkanoyl L-carnitine inner salt in aqueous solution;
(c) distilling the step (b) L-carnitine or alkanoyl L-carnitine inner salt solution until an aqueous solution is obtained containing 60% weight by weight of L-carnitine inner salt or alkanoyl L-carnitine inner salt;
(d) adding to the step (c) solution a suitable amount of mucic acid to yield a solution in which the mucic acid is dissolved together with the L-carnitine or alkanoyl L-carnitine;
(e) adding to the step (d) solution a suitable amount of organic solvent as a precipitating agent; wherein two liquid phases are transformed under stirring into a suspension of the inner salt;
(f) isolating the step (e) precipitate; and optionally
(g) drying the step (f) precipitate.

2. The process according to claim 1, in which the alkanoyl L-carnitine chloride is selected from the group consisting of acetyl L-carnitine chloride, and propionyl L-carnitine chloride.

3. The process according to claim 1 or 2, in which the precipitating agent is selected from the group consisting of acetone, isobutyl alcohol, tetrahydrofuran, ethyl acetate, and ethyl acetoacetate.

* * * * *

UNITED STATES PATENT AND TRADEMARK OFFICE
CERTIFICATE OF CORRECTION

PATENT NO.    : 6,693,215 B2
DATED         : February 17, 2004
INVENTOR(S)   : Bagolini et al It is certified that error appears in the above-identified patent and that said Letters Patent is hereby corrected as shown below:

Title page,
Insert Item: -- [30], Foreign Application Priorty Data
            February 10 2000 (IT) ............................. RM2000A000060 --

Signed and Sealed this

Twenty-seventh Day of July, 2004

JON W. DUDAS
*Acting Director of the United States Patent and Trademark Office*